United States Patent [19]

Rutter

[11] 4,404,017
[45] Sep. 13, 1983

[54] PHTHALIMIDOGUANIDINE PLANT GROWTH REGULATORS

[75] Inventor: Jerry L. Rutter, Mentor, Ohio

[73] Assignee: Gulf Oil Corporation, Pittsburgh, Pa.

[21] Appl. No.: 165,917

[22] Filed: Jul. 3, 1980

[51] Int. Cl.³ .................... A01N 43/38; A01N 43/40; A01N 43/84; A01N 47/44
[52] U.S. Cl. .......................................... 71/88; 71/76; 71/94; 71/96; 544/144; 548/475; 546/281
[58] Field of Search ................... 260/326 N; 544/144; 546/273, 201; 71/96, 76, 88, 94

[56] References Cited

U.S. PATENT DOCUMENTS

| | | | |
|---|---|---|---|
| 3,267,097 | 8/1966 | Kuhle et al. | 71/94 |
| 3,284,289 | 11/1966 | Duerr et al. | 71/94 |
| 4,073,636 | 2/1978 | Regel et al. | 71/94 |

OTHER PUBLICATIONS

"Internation Encyclopedia of Science" p. 19.
Kingzett's Chemical Encyclopedia, p. 18.
Hackh's Chemical Dictionery, 3rd Ed., p. 18.

*Primary Examiner*—Mark L. Berch
*Attorney, Agent, or Firm*—Deane E. Keith; Forrest D. Stine

[57] ABSTRACT

Novel compounds are disclosed which have utility as plant growth regulators. Use to produce growth regulators is specifically illustrated. The novel compounds of this invention are phthalimidoguanidines of the following general structural formulas:

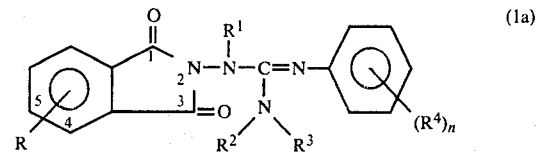

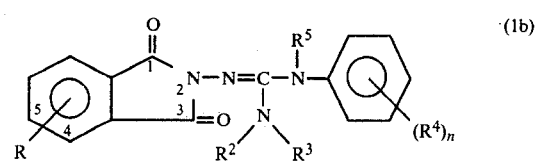

in which R, $R^1$ and $R^5$ are hydrogen or $C_1$ to $C_5$ alkyl, $R^2$ and $R^3$ are alike or unlike, one of which may be hydrogen but otherwise are substituents selected from $C_1$ to $C_5$ alkyl, alkenyl or alkynyl, branches or unbranched, $C_2$ to $C_5$ hydroxyalkyl or alkoxyalkyl, $C_3$ to $C_5$ cycloalkyl, furfuryl, pyridyl, benzyl, phenyl, $C_1$ to $C_5$ alkylphenyl, or $-NR^2R^3$ together may be 2,5-dimethyl-1-pyrryl, 4-morpholinyl or 1-pyrrolidinyl, $R^4$ is halogen, nitro, cyano, trifluoromethyl, $C_1$ to $C_5$ alkyl or acyl and n is zero, one or two.

11 Claims, No Drawings

PHTHALIMIDOGUANIDINE PLANT GROWTH REGULATORS

DESCRIPTION OF THE INVENTION

This invention is directed to a novel group of chemical substances which have, to a high degree the ability to change or modify the growth habits of plants. The invention is also directed to methods of regulating growth of plants to obtain desirable modifications, in particular the increase of fruit set, by application to living plants, their seeds, or to the soil of effective amounts of the novel compounds. Also are included methods of manufacturing the compounds, as well as agricultural formulations containing the novel compounds as growth regulators.

Briefly, the novel compounds of this invention are phthalimidoguanidines of the following general structural formulas:

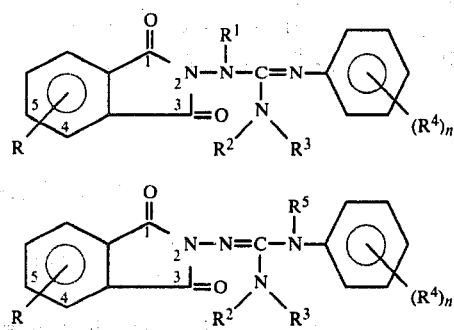

in which R, $R^1$ and $R^5$ are hydrogen or $C_1$ to $C_5$ alkyl, $R_2$ and $R^3$ are alike or unlike, one of which may be hydrogen but otherwise are substituents selected from $C_1$ to $C_5$ alkyl, alkenyl or alkynyl, branched or unbranched, $C_2$ to $C_5$ hydroxyalkyl or alkoxyalkyl, $C_3$ to $C_5$ cycloalkyl, furfuryl, pyridyl, benzyl, phenyl, $C_1$ to $C_5$ alkylphenyl, or $-NR^2R^3$ together may be 2,5-dimethyl-1-pyrryl, 4-morpholinyl or 1-pyrrolidinyl, $R^4$ is halogen, nitro, cyano, trifluoromethyl, $C_1$ to $C_5$ alkyl or acyl and n is zero, one or two.

Synthesis of the Growth Regulators

The compounds of this invention are readily prepared from the corresponding isothioureido isoindoldiones by reaction with amines, as illustrated by the following procedure.

Preparation of 1,1,3-Trimethyl-3-phthalimido-2-phenylguanidine

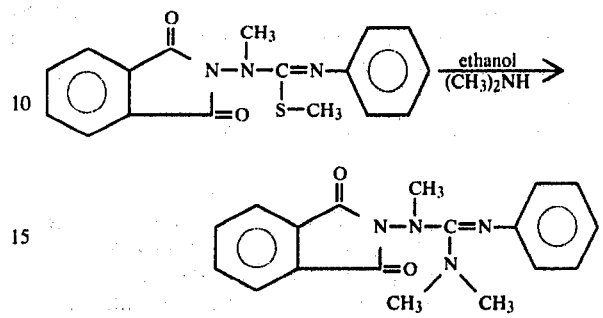

To a saturated solution of anhydrous dimethylamine in 80 ml. of ethanol was added 4.53 g. (0.01 mol) of 2-(1,2-dimethyl-3-phenylisothioureido)-1H-isoindole-1,3-(2H)-dione, and the resulting solution was heated to 50° C. for 30 minutes. Evaporation and treatment with heptane gave 3.5 g. of crystalline product, m.p. 146°-8° C.

The isothioureido isoindolediones employed as starting materials for the foregoing illustrative procedure may be manufactured by means of the general method comprising reacting a compound of the formula:

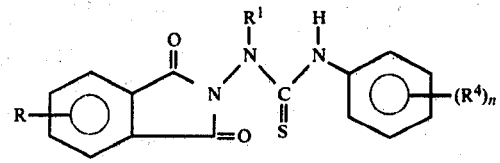

in a non-reactive polar organic solvent with a compound of the formula R-X in which X is a leaving group exemplified by a chlorine, bromine, iodine or sulfate substituent. Specific procedures which are suitable for synthesis of representative compounds are outlined in the following chart and exemplified below.

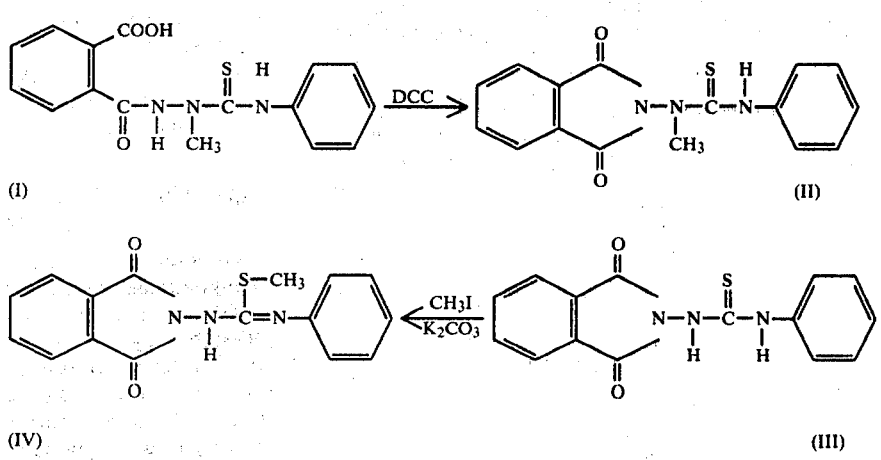

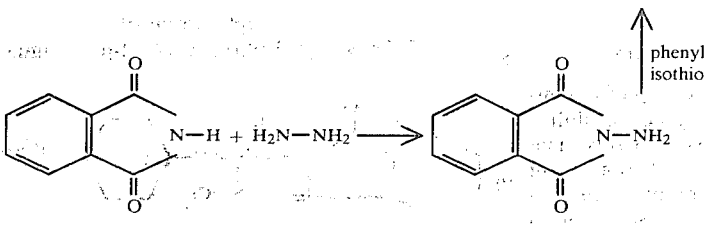

It will be understood that when it is desired that R and R¹ shall be different, the alkylation at the sulfur and amino locations is conveniently done in separate reaction steps. The following specific procedures illustrate the general methods of synthesis. All temperatures in the procedures are in °C.

Synthesis of methyl hydrogen phthalate

Methanol (300 ml) was added in a single portion to 148 g (1.00 mole) of phthalic anhydride and the resulting suspension was stirred and heated at reflux for 36 hours; solution occurred during heating. The solvent was removed and the product was recrystallized from a mixture of ethyl acetate and hexane to afford 114.6 g of the title compound (Lit.: Beilstein, 9,797-mp 82.5°, 84°).

Synthesis of methyl phthaloyl chloride

Methyl hydrogen phthalate (110.0 g., 0.611 mole) and thionyl chloride (77.4 g., 0.650 mole) were mixed in 200 ml of chloroform, keeping the temperature below 30°. After stirring for two hours at room temperature, the system was heated at reflux for five hours. The solvent was evaporated at reduced pressure and the crude product (120.9 g) was used without further purification (Lit.: Beilstein, 9, 797-no constants).

Synthesis of 2-(2-carboxybenzoyl)-1-methyl-N-phenylhydrazinethiocarboxamide (I)

This compound was made by reacting phthalic anhydride with 1-methyl-N-phenylhydrazinethiocarboxamide according to conventional procedures, as follows:

The hydrazinethiocarboxamide was dissolved in about 75 ml of dimethylformamide and placed in a 3-necked round-bottomed flask equipped with magnetic stirrer, condenser, additional powder funnel and thermometer. The anhydride was added in portions at 20°. The contents were stirred overnight at room temperature, then poured into ice water the following morning. The resulting solid was recrystallized in hexane and ethanol (m.p. 155°-156° C.).

Optionally ring substituted phthalic anhydrides and substituted 2-carbomethoxybenzoyl chlorides may be condensed with substituted 1-methylhydrazinethiocarboxamides to give desired intermediate compounds as in the following scheme:

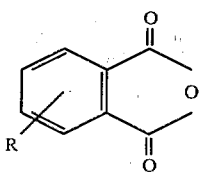

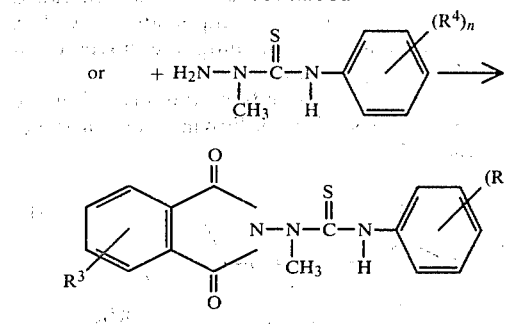

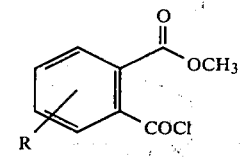

These methods are illustrated in the following specific procedures. The identity of the product was confirmed in each instance by means of infrared and nuclear magnetic resonance spectra. All melting points are as determined, uncorrected (Degrees C.).

N-Methyl-N-(phenylthiocarbamoyl)-2-amino-1H-isoindole-1,3-(2H)dione (II)

To an ice-cold solution of 8.25 g (0.025 mole) of 2-(2-carboxybenzoyl)-1-methyl-N-phenylhydrazinethiocarboxamide in 225 ml of 1,2-dimethoxyethane at ~2° C., a solution of 5.5 g (0.027 mole) of N,N'-dicyclohexylcarbodiimide was added dropwise below 5° C. with stirring. The mixture was stirred in the ice bath and then left at room temperature overnight. The mixture was filtered to remove N,N'-dicyclohexylurea and the filtrate was evaporated below 40° C., under vacuum, to give a yellow amorphous solid which was stirred in 100 ml of dry ether and warmed gently. The ether solution was allowed to stand for a few hours and filtered to give 4.6 g (59%) of whitish yellow crystals, m.p. 142°-144°.

Recrystallization from ethyl acetate-hexane gave whitish crystals, m.p. 151°-153°.

Mass spectrum: M+311.

N-Methyl-N(phenylthiocarbamoyl)-2-amino-4-methyl-1H-isoindole-1,3-(2H)dione

To a solution of 6.8 g (0.037 mole) of 1-methyl-N-phenylhydrazinethiocarboxamide and 3.0 g of pyridine in 100 ml dry dimethoxyethane, 2-carbomethoxy-6-methylbenzoyl chloride (8.0 g, 0.037 mole) was added and the resulting mixture was stirred at room temperature for 60 hours. The solvent was distilled and the residue was taken up in ethyl acetate, filtered and dried on anhydrous magnesium sulfate. Removal of the solvent gave 10 g (83%) of the desired product, m.p. 110°–115° (dec.).

2-Amino-1H-isoindole-1,3-(2H)dione

To an ice-cold suspension of 14.7 g (0.1 mole) of phthalimide in 100 ml of 95% ethyl alcohol at 5° C., with stirring, 3.6 ml (0.11 mole) of 96.8% hydrazine was added dropwise. A slight exothermic reaction was observed and the mixture was allowed to stir at 5° C. for two hours. The mixture was diluted with 200 ml of ice water, stirred, filtered, washed with water and dried to give 12.2 g (75%) of white powder, m.p. 199°–202°.

Recrystallization from methanol-water gave white needles, m.p. 201°–203°.

N-(Phenylthiocarbamoyl)-2-amino-1H-isoindole-1,3-(2H)dione (III)

To a suspension of 8.2 g (0.05 mole) of 2-amino-1H-isoindole-1,3-(2H)dione in 50 ml of dry 2-propanol, 6 ml (0.05 mole) of phenyl isothiocyanate was added. The mixture was stirred and refluxed for 3 hours, allowed to cool to room temperature and poured into 300 ml of 50% ethyl alcohol. After stirring for one hour, the solid which formed was filtered, washed with water and dried to give 12.1 g (81%) of the desired product as a white powder, m.p. 180°–181°. To make compounds in which Ar is benzoyl, benzoyl isothiocyanates may be employed in procedures of the type described above.

The free base was obtained by suspending the salt in dilute $NH_4OH$ and extracting with $CHCl_3$ which was washed with water, then with saturated aqueous NaCl and dried over anhydrous $Na_2SO_4$. Removal of the $CHCl_3$ at reduced pressure in a rotary evaporator gave a residual oil which was crystallized from ether-petroleum ether, wt. 4.6 g, m.p. 90°–91° (75%).

Preparation of 2-(2-Methyl-3-phenylisothioureido)-1H-isoindole-1,3-(2H)-dione (IV)

To 100 ml of dry acetone, 5.0 g (0.018 m) of N-(phenylthiocarbamoyl)-2-amino-1-H-isoindole-1,3-(2H)dione and 2.5 g (0.018 m) powdered anhydrous potassium carbonate was added. To this suspension 1.1 ml (0.018 m) of methyl iodide was added and the mixture was stirred overnight at room temperature. The mixture was poured into ~300 ml of water, stirred, filtered, washed with water and dried to give 4.4 g (78%) of a yellow powder, m.p. 161°–164°. Mass spectrum: M+311.

Preparation of 2-(1-Allyl-2-methyl-3-phenylisothioureido)-1-H-isoindole-1,3-(2H)dione To 50 ml of dry acetone, 4.0 g (0.013 m) of the above product (IV), 2.2 g (0.016 m) of powdered anhydrous potassium carbonate, and 1.4 ml (0.016 m) of allyl bromide was added in succession and the mixture stirred overnight at room temperature. The mixture was poured into 300 ml of ice water with stirring. The aqueous layer was decanted and the residue suspended in fresh ice cold water, stirred and filtered to give a yellow semisolid product. This was purified by stirring in hexane to give a yellow powder 1.8 g (39%), m.p. 78°–81°.

Compounds which have been made by means of the foregoing illustrative procedures are listed in Table 1 below.

TABLE 1

COMPOUNDS OF THE FORMULAS:

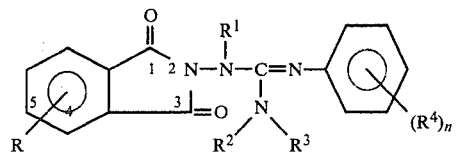
(1a)

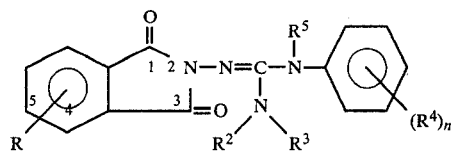
(1b)

| No. | m.p. °C. | R | $R^1$ | $-NR^2R^3$ | $(R^4)_n$ | $R^5$ |
|---|---|---|---|---|---|---|
| 4368 | oil | H | $CH_3$ | $-N(C_2H_5)_2$ | n = 0 | — |
| 4646 | 146-8° | " | " | $-N(CH_3)_2$ | " | — |
| 4647 | 192-5° | " | " | 4-morpholinyl | " | — |
| 4648 | oil | " | " | -1-piperidyl | " | — |
| 4649 | 159-61° | " | " | -1-pyrrolidinyl | " | — |
| 4650 | oil | " | " | —N—methyl benzyl | " | — |
| 4651 | oil | " | " | —N—isopropyl benzyl | " | — |
| 4652 | oil | " | " | —N—methyl phenyl | " | — |
| 4653 | oil | " | " | —N—ethyl phenyl | " | — |
| 4654 | oil | " | " | $-N(CH_2CH_2CH_3)_2$ | " | — |
| 4655 | oil | " | " | $-N(CH-CH_3)_2$ with $CH_3$ substituent | " | — |
| 4656 | oil | " | " | $-N(CH_2CH_2CH_2CH_3)_2$ | " | — |
| 4657 | oil | " | " | —N propyl phenyl | " | — |
| 4658 | oil | " | " | $-N(sec.butyl)_2$ | " | — |
| 4659 | oil | " | " | $-N(CH_2CH_2CH_2CH_2CH_3)_2$ | " | — |
| 4660 | oil | " | " | $-N(allyl)_2$ | " | — |
| 4661 | oil | " | " | $-N(nonyl)_2$ | " | — |

TABLE 1-continued

COMPOUNDS OF THE FORMULAS:

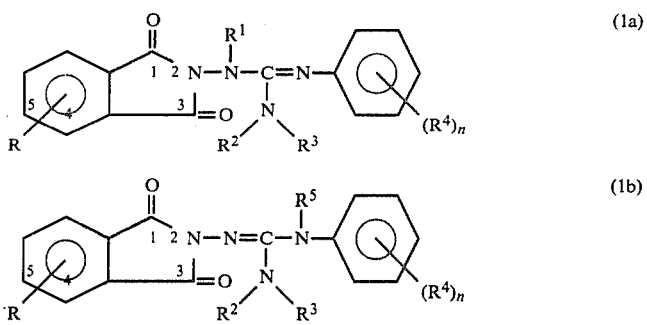

(1a)

(1b)

| No. | m.p. °C. | R | $R^1$ | $-NR^2R^3$ | $(R^4)_n$ | $R^5$ |
|---|---|---|---|---|---|---|
| 4702 | oil | " | " | $-N(isobutyl)_2$ | " | — |
| 4703 | oil | " | " | $-N-$methyl cyclooctyl | " | — |
| 4704 | oil | " | " | $-N(octyl)_2$ | " | — |
| 4705 | oil | " | " | $-N-$methyl propyl | " | — |
| 4707 | oil | " | " | $-N-$propyl isopropyl | " | — |
| 4708 | oil | " | " | $-N-$propyl isobutyl | " | — |
| 4709 | oil | " | " | $-N-$propyl sec.butyl | " | — |
| 4710 | oil | " | " | $-N-$propyl butyl | " | — |
| 4716 | oil | " | " | $-N-$benzyl 2-propynyl | " | — |
| 4717 | oil | " | " | $-N-$allyl phenyl | " | — |
| 4718 | oil | " | " | $-N-$ethyl p-tolyl | " | — |
| 4719 | 233–5° | " | " | $-N(CH_3)_2$ | 3-F | — |
| 4720 | oil | " | " | -4-morpholinyl | " | — |
| 4721 | 190–191° | " | " | $-NH-CH_2CH_2CH_2CH_3$ | n = 0 | — |
| 4722 | 136–8° | " | " | $-NH-$allyl | " | — |
| 4723 | 137–40° | " | " | $-NH-$benzyl | " | — |
| 4724 | 154–165° | " | " | $-NH-(CH_2)_3CH_3$ | 3-F | — |
| 4725 | 52–3° | " | " | $-NH-C(CH_3)_3$ | n = 0 | — |
| 4726 | 190–191° | " | " | $-NH-CH_2CH_2CH_3$ | " | — |
| 4727 | 185–95° | " | " | $-NH-$cyclopropyl | " | — |
| 4728 | oil | " | " | $-NH-$cyclopentyl | " | — |
| 4739 | 52–4° | " | " | $-N(CH_3)(CH_2CH_2OH)$ | " | — |
| 4740 | glass | " | " | $-N(CH_3)_2$ | 2,5-$(CH_3)_2$ | — |
| 4741 | 82–5° | " | " | $-N(CH_3)_2$ | 4-$NO_2$ | — |
| 4742 | oil | " | " | $-N(CH_3)_2$ | 4-F | — |
| 4743 | 148–152° | " | " | $-N(CH_3)_2$ | 4-CN | — |
| 4756 | 103–5° | " | " | $-N(CH_3)_2$ | 4-$CF_3$ | — |
| 4757 | 137–9° | " | " | $-N(CH_3)_2$ | 2,4-$Cl_2$ | — |
| 4758 | glass | " | " | $-N(CH_3)_2$ | 3-$COCH_3$ | — |
| 4759 | glass | " | — | $-N(CH_3)_2$ | n = 0 | $-C_2H_5$ |
| 4760 | glass | " | — | $-N(CH_3)_2$ | n = 0 | $-CH_3$ |
| 4762 | 164–72° | " | H | $-N(CH_3)_2$ | 3-F | — |
| 4764 | oil | " | $CH_3$ | 1-pyrrolidinyl | " | — |
| 4850 | oil | 4-$CH_3$ | $CH_3$ | $-NH(CH_2)_3CH_3$ | n = 0 | — |
| 4956 | oil | H | " | $-NH-CH_2CH_2OCH_3$ | " | — |
| 4957 | oil | " | " | $-N-$methyl furfuryl | " | — |
| 4958 | oil | " | " | -2,5-dimethyl-1-pyrryl | " | — |
| 4959 | oil | " | " | $-NH-$2-pyridyl | " | — |

Use of the Growth Regulators

In highly active compounds, phytotoxic and growth-altering effects of pre-emergent and post-emergent application are often readily apparent. These effects may be demonstrated by means of the following illustrative procedures.

Pre-emergent Application

Disposable paper trays about 2 1.2 inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulant compound in 15 ml. of acetone, adding 4 ml. of a solvent-emulsifier consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml. by addition of warm water. Twenty-one days after seeding and treatment the plantings were examined and plant injury was rated according to the following schedule.

DEGREE OF EFFECT

0 = no effect,
1 = slight effect, plants recovered,
2 = moderate effect, injury to 26 to 75 percent,
3 = severe effect, injury to 76 to 99 percent, of foliage,
4 = maximum effect (all plants died).

Post-emergent Application

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulant. Plant injury was again rated according to the schedule disclosed above.

Observations of growth regulant effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |
| Chlorosis | C |

In the table below there are tabulated the observations of pre- and post-emergent herbicidal and growth regulator effects resulting from use of one of the growth regulators of this invention according to the procedures set forth above.

total volume up to 80 ml by addition of warm water. Of this spray mixture, a 50 ml portion was used to spray the plants at a rate of 3 lb. per acre of sprayed area. The remaining 30 ml. was diluted to 90 ml. with warm water and was used to spray the plants at a rate of 1 lb. per acre. One large, more mature tomato plants was included in the test along with the other, smaller growing plants. For comparative purposes, plants were also sprayed at a spray volume of 40 gallons per acre with a spray mixture containing no growth regulator.

Approximately fifteen days after spraying, the plants were observed and the results were evaluated according to the schedule disclosed above. Results obtained with representative compounds are presented in Table 3. The test species are as follows:

| Number | Common Name | Scientific Name |
|---|---|---|
| I | Pigweed | *Amaranthus retroflexus* |
| II | Lambsquarters | *Chenopodium album* |
| III | Crabgrass | *Digitaria sanguinalis* |
| IV | Downey brome | *Bromus tectorum* |
| V | Giant foxtail | *Setaria faberii* |
| VI | Nutsedge | *Cyperus esculentus* |
| VII | Peanuts | *Arachis hypogaea* |
| VIII | Cotton | *Gossypium herbaceum* |

TABLE 2

EFFECTS OF THE COMPOUNDS ON PLANT SPECIES

| | Pre-emergent Effects | | | | | | Post-emergent Effects | | | | | |
|---|---|---|---|---|---|---|---|---|---|---|---|---|
| Compound No. | *Digitaria sanguinalis* | *Celosia plumosa* | *Bromus inermis* | *Setaria italica* | *Raphanus sativus* | *Beta vulgaris* | *Setaria italica* | *Medicago sativa* | *Avena sativa* | *Raphanus sativus* | *Beta vulgaris* | *Lycopersicum esculentum* |
| 4368 | F3G3 | K4 | F3G3 | F3G3 | F3G3 | F3G3 | F1G1 | F3G2 | F2G1 | G1 N2F1 | F3G2 | F3G1 |

Post-emergent Application at Lower Rates on 24 Species

Twenty-four species of plants were grown in potting soil in disposable styrofoam trays and tomatoes were grown in four-inch pots in the greenhouse. Aqueous spray formulations were prepared and the growing plants were sprayed at a spray volume of 40 gallons per acre and application rates of 3 lb. and 1 lb. per acre. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing

| Number | Common Name | Scientific Name |
|---|---|---|
| IX | Tomato | *Lycopersicum esculentum* |
| X | Sugar beets | *Beta vulgaris* |
| XI | Wild buckwheat | *Polygonum convolvulus* |
| XII | Wild mustard | *Brassica kaber* |
| XIII | Mature tomato plant | *Lycopersicum esculentum* |
| XIV | Cocklebur | *Xanthium pensylvanicum* |
| XV | Morning glory | *Ipomea purpurea* |
| XVI | Soybeans | *Soja max* |
| XVII | Barnyard grass | *Echinochloa crusgalli* |
| XVIII | Green foxtail | *Setaria viridis* |
| XIX | Alfalfa | *Medicago sativa* |
| XX | Corn | *Zea mays* |
| XXI | Grain sorghum | *Sorghum vulgare* |
| XXII | Shattercane | *Sorghum bicolor* |
| XXIII | Wheat | *Triticum aestivum* |
| XXIV | Wild oats | *Avena fatua* |
| XXV | Rice | *Oryza sativa* |

TABLE 3

POST-EMERGENT EFFECTS ON 24 SPECIES

| Species | Appl'n. Rate (lb/A) | Compound Nos. | | | | | |
|---|---|---|---|---|---|---|---|
| | | 4646 | 4677 | 4648 | 4649 | 4650 | 4651 |
| I | 3 | F2G2 | F3G3 | F3G3 | F3G3 | F3G3 | F3G3 |
| | 1 | F1 | F3G3 | F3G3 | F3G2 | F3G3 | F3G3 |
| II | 3 | F2G2 | F3G3 | F3G3 | F3G3 | F3G3 | F3G3 |
| | 1 | F1 | F2G2 | F3G3 | F1G1 | F3G3 | F3G3 |
| III | 3 | 0 | F1 | F2G2 | G1 | F3G3 | F2G1 |
| | 1 | 0 | 0 | F1G1 | 0 | F1 | F2G1 |
| IV | 3 | 0 | 0 | F1 | 0 | F1G1 | 0 |
| | 1 | 0 | 0 | 0 | 0 | 0 | 0 |
| V | 3 | 0 | F1 | F3G3 | F1 | F3G3 | F1G1 |
| | 1 | 0 | 0 | F2G2 | 0 | F1 | F1G1 |
| VI | 3 | 0 | 0 | 0 | 0 | F1 | 0 |
| | 1 | 0 | 0 | 0 | 0 | 0 | 0 |
| VII | 3 | 0 | 0 | 0 | 0 | F1 | F1 |
| | 1 | 0 | 0 | 0 | 0 | 0 | 0 |
| VIII | 3 | 0 | F2 | F1 | F2G2 | F3G3 | F3G1 |

TABLE 3-continued
POST-EMERGENT EFFECTS ON 24 SPECIES

|     |     |     |     |     |     |     |     |
| --- | --- | --- | --- | --- | --- | --- | --- |
|     | 1   | 0   | F1  | F1  | F1  | F2G1 | F2G1 |
| IX  | 3   | F2  | G2F3 | F3G3 | F3G3 | F3G3 | F3G3 |
|     | 1   | F1  | F3  | F3G3 | F3  | F3G2 | F3G2 |
| X   | 3   | F2  | F1G1 | F3G3 | F2G2 | F3G3 | F3G3 |
|     | 1   | F1  | F1  | F3G3 | F1  | F2G1 | F2G1 |
| XI  | 3   | 0   | 0   | F2G2 | F1G1 | F2G2 | F3G2 |
|     | 1   | 0   | 0   | F2G1 | 0   | F1  | F1  |
| XII | 3   | F1  | F1  | F3G2 | F1  | F2G2 | F3G3 |
|     | 1   | 0   | 0   | F3G2 | 0   | F1  | C2F1 |
| XIII | 3  | F1  | F2  | F3  | F3  | F3G1 | F3  |
|     | 1   | F1  | F2  | F3  | F2  | F3  | F3  |
| XIV | 3   | F1  | 0   | F2G1 | F1  | F2G2 | F2  |
|     | 1   | 0   | 0   | F1  | 0   | F2G1 | F1  |
| XV  | 3   | F1  | F2  | F2G2 | —   | F3G3 | F3G2 |
|     | 1   | 0   | F1  | F1G1 | 0   | F2G2 | F2G1 |
| XVI | 3   | F2  | G2F2 | F3G3 | F2  | F3G3 | F3G3 |
|     | 1   | F1  | F2G1 | F3G3 | F1  | F3G3 | F3G2 |
| XVII | 3  | 0   | 0   | F1  | 0   | F1G1 | F1  |
|     | 1   | 0   | 0   | F1  | 0   | F1  | 0   |
| XVIII | 3 | 0   | F1  | F2G1 | F1  | F2G2 | F2G2 |
|     | 1   | 0   | 0   | F1  | 0   | F1G1 | F1G1 |
| XIX | 3   | F1  | F2  | F3G3 | F2  | F3G3 | F3G3 |
|     | 1   | 0   | F1  | F3G2 | F1  | F3G2 | F3G1 |
| XX  | 3   | 0   | 0   | C1  | 0   | F1  | 0   |
|     | 1   | 0   | 0   | 0   | 0   | 0   | 0   |
| XXI | 3   | 0   | F1  | F1  | 0   | F2  | F2  |
|     | 1   | 0   | 0   | 0   | 0   | F1  | F1  |
| XXII | 3  | 0   | F1  | F1  | 0   | F2  | F2  |
|     | 1   | 0   | 0   | 0   | 0   | 0   | F1  |
| XXIII | 3 | 0   | F1  | 0   | 0   | F1  | F1  |
|     | 1   | 0   | 0   | 0   | 0   | 0   | F1  |
| XXIV | 3  | 0   | 0   | 0   | 0   | F1  | F1  |
|     | 1   | 0   | 0   | 0   | 0   | 0   | 0   |
| XXV | 3   | 0   | 0   | 0   | 0   | F1  | F1  |
|     | 1   | 0   | 0   | 0   | 0   | 0   | 0   |
| Comments |  | increased fruit set | increased fruit set | more fruit set | more fruit set | more fruit set, tillers | more fruit set, tillers |

| Species | Appl'n. Rate (lb/A) | 4652 | 4653 | 4654 | 4655 | 4656 | 4657 |
| --- | --- | --- | --- | --- | --- | --- | --- |
| I   | 3   | F3G3 | F3G3 | F3G3 | F3G3 | F3G3 | F3G3 |
|     | 1   | F3G3 | F3G3 | F3G3 | F3G3 | F3G3 | F3G3 |
| II  | 3   | F3G3 | F3G3 | F3G3 | F3G3 | F3G3 | F3G3 |
|     | 1   | F3G3 | F3G3 | F3G3 | F3G2 | F3G3 | F3G3 |
| III | 3   | F3G2 | F3G2 | F1  | G1F1 | F2G1 | F1G1 |
|     | 1   | F1G1 | F1  | F1  | F1  | F1G1 | F1  |
| IV  | 3   | F1  | F1  | 0   | 0   | F1  | 0   |
|     | 1   | 0   | 0   | 0   | 0   | 0   | 0   |
| V   | 3   | F2  | F3G2 | F2G1 | F2G1 | F2G2 | F2G2 |
|     | 1   | F2  | F2G1 | F2  | F2G1 | F1  | F1  |
| VI  | 3   | 0   | 0   | 0   | 0   | 0   | 0   |
|     | 1   | 0   | 0   | 0   | 0   | 0   | 0   |
| VII | 3   | F1  | F1  | F1  | 0   | F1  | F1  |
|     | 1   | 0   | 0   | 0   | 0   | 0   | 0   |
| VIII | 3  | F2G1 | F2G1 | F2  | F1  | F3G3 | F2G1 |
|     | 1   | F2  | F2  | F2  | F1  | F2  | F1  |
| IX  | 3   | F3G3 | F3G3 | F3G3 | F3G3 | F3G3 | F3G3 |
|     | 1   | F3G3 | F3G3 | F3G3 | F3G3 | F3G3 | F3G3 |
| X   | 3   | F3G3 | F3G2 | F3G2 | F3G3 | F3G3 | F3G3 |
|     | 1   | F3G2 | F3G2 | F3G2 | F3G2 | F2G2 | F2G2 |
| XI  | 3   | F2G2 | F2G2 | F2G2 | F2G2 | F2G2 | F2G2 |
|     | 1   | F1G1 | F1  | F2  | F1  | F1G1 | F1  |
| XII | 3   | F2G2 | F3G2 | F2G2 | F3G2 | F2G2 | F2G1 |
|     | 1   | C2F1 | C2F1 | F2G1 | C1F1 | F1C2 | F1C1 |
| XIII | 3  | F3G2 | F3G3 | F3G3 | F3G3 | F3G3 | F3G3 |
|     | 1   | F3  | F3G2 | F3G1 | F3G2 | F3G2 | F3G3 |
| XIV | 3   | F2G1 | F2G1 | F2G1 | F2G1 | F2G1 | F3G2 |
|     | 1   | F1  | F1  | —   | F1  | F1G1 | F1  |
| XV  | 3   | F3G2 | F3G3 | F3G3 | F3G3 | F3G3 | F3G3 |
|     | 1   | F3G2 | G2F2 | F2G1 | F2G2 | F3G2 | F2G1 |
| XVI | 3   | F3G3 | F3G3 | F3G3 | F3G3 | F3G3 | F3G3 |
|     | 1   | F3G2 | F3G2 | F3G2 | F3G2 | F3G2 | F3G3 |
| XVII | 3  | F2G1 | F2G1 | F1G1 | F1  | F1  | F1  |
|     | 1   | F1  | F1  | 0   | 0   | 0   | 0   |
| XVIII | 3 | F2G2 | F3G2 | F2G2 | F2G2 | F2G2 | F2G2 |
|     | 1   | F2G2 | F3G2 | F2G2 | F2G1 | F1G1 | F2G1 |
| XIX | 3   | F3G3 | F3G3 | F3G2 | F3G3 | F3G3 | F3G3 |

TABLE 3-continued

POST-EMERGENT EFFECTS ON 24 SPECIES

| Species | | | | | | | |
|---|---|---|---|---|---|---|---|
| | 1 | F3G2 | F3G2 | F3G1 | F3G1 | F3G2 | F3G1 |
| XX | 3 | F1 | F2G1 | F1 | F1 | F1G1 | F1 |
| | 1 | 0 | F1 | 0 | 0 | 0 | 0 |
| XXI | 3 | F3G1 | F3G2 | F2G1 | F1 | F2G1 | F2G1 |
| | 1 | F1 | F1 | F1 | F1 | 0 | F1 |
| XXII | 3 | F3G1 | F3G2 | F2G1 | F1 | F2G1 | F2G1 |
| | 1 | F1 | F1 | F1 | F1 | F1 | F1 |
| XXIII | 3 | F2G1 | F1G1 | F1 | 0 | F1 | F1 |
| | 1 | 0 | 0 | 0 | 0 | 0 | 0 |
| XXIV | 3 | F1G1 | F1 | F1 | 0 | F1 | F1 |
| | 1 | 0 | 0 | 0 | 0 | 0 | 0 |
| XXV | 3 | F1G1 | F1 | F1 | 0 | F1 | F1 |
| | 1 | 0 | 0 | 0 | 0 | 0 | 0 |
| Comments | | more fruit set | more tillers | more tillers | | more tillers | |

| Species | Appl'n. Rate (lb/A) | Compound Nos. | | | | | |
|---|---|---|---|---|---|---|---|
| | | 4658 | 4659 | 4660 | 4661 | 4702 | 4703 |
| I | 3 | F3G3 | F3G3 | F3G3 | F3G3 | C3G3 | F1 |
| | 1 | F3G3 | F3G3 | F3G2 | F3G3 | F3G2 | F1 |
| II | 3 | F3G3 | F3G3 | F3G3 | F3G3 | C3G3 | F1 |
| | 1 | F3G3 | F3G3 | F3G2 | F3G3 | F3G3 | F1 |
| III | 3 | F2G2 | F1G1 | G2F1 | F3G2 | G2F2 | 0 |
| | 1 | F1G1 | F1 | G1 | F2G1 | F1 | 0 |
| IV | 3 | F1 | 0 | G1 | G1 | G1 | 0 |
| | 1 | 0 | 0 | 0 | 0 | 0 | 0 |
| V | 3 | F2G2 | F1 | F2G2 | F3G2 | F3G2 | 0 |
| | 1 | F1 | 0 | F1 | F2G1 | F1 | 0 |
| VI | 3 | 0 | 0 | 0 | 0 | 0 | 0 |
| | 1 | 0 | 0 | 0 | 0 | 0 | 0 |
| VII | 3 | F1 | 0 | F1 | F1 | 0 | 0 |
| | 1 | 0 | 0 | 0 | 0 | 0 | 0 |
| VIII | 3 | F2G1 | F2G1 | F3G3 | F2G1 | F1 | 0 |
| | 1 | F1 | F1 | F1 | F1 | 0 | 0 |
| IX | 3 | F3G3 | F3G3 | F3G3 | F3G3 | F3G3 | F2 |
| | 1 | F3G3 | F3G3 | F3G3 | F3G3 | F3G1 | F2 |
| X | 3 | F3G2 | F3G3 | F3G2 | F3G3 | F3G2 | F1 |
| | 1 | F3G2 | F3G2 | F3G2 | F3G2 | F2 | F1 |
| XI | 3 | F2G2 | F2G1 | F1G1 | F1G1 | F1 | 0 |
| | 1 | F1G1 | F1 | F1 | F1 | 0 | 0 |
| XII | 3 | F2G2 | F2G1 | F3G2 | F3G3 | C2F1 | 0 |
| | 1 | F1C1 | F1 | G1F1 | F1G1 | 0 | 0 |
| XIII | 3 | F3G3 | F3G3 | F3G3 | F3G3 | F3G1 | F3 |
| | 1 | F3G3 | F3G2 | F3 | F3 | F3 | F2 |
| XIV | 3 | F2G2 | F2G1 | F2G1 | F2 | F1 | F1 |
| | 1 | F1 | F1 | F2 | F1 | F1 | F1 |
| XV | 3 | F3G3 | F3G3 | F3G2 | F3G3 | F3G2 | F2G2 |
| | 1 | F3G3 | F3G3 | F3G1 | F3G2 | F1 | F1 |
| XVI | 3 | F3G3 | F3G3 | F3G3 | F3G3 | F3G2 | F3G2 |
| | 1 | F3G3 | F3G2 | F3G3 | F3G3 | F3G2 | F2G2 |
| XVII | 3 | F1 | F1 | F1 | F1 | 0 | 0 |
| | 1 | 0 | 0 | 0 | 0 | 0 | 0 |
| XVIII | 3 | F2G2 | F2G2 | F2G1 | F2G2 | F2G1 | 0 |
| | 1 | F2G1 | F1 | F1G1 | F1 | F1 | 0 |
| XIX | 3 | F3G3 | F3G3 | F3G2 | F3G3 | F3G2 | F2C1 |
| | 1 | F3G2 | F3G1 | F3G2 | F3G1 | C1F2 | F1 |
| XX | 3 | F1 | F1 | F1 | F1 | F1 | 0 |
| | 1 | F1 | 0 | 0 | 0 | 0 | 0 |
| XXI | 3 | F2G1 | F2 | F2G1 | F2G1 | F2 | F1 |
| | 1 | F2 | 0 | F1 | F1 | F1 | 0 |
| XXII | 3 | F2G1 | F2 | F2G1 | F2G1 | F2 | F1 |
| | 1 | F2 | 0 | F1 | F1 | F1 | 0 |
| XXIII | 3 | F1 | F1 | F1 | F1 | F1 | 0 |
| | 1 | F1 | 0 | 0 | 0 | 0 | 0 |
| XXIV | 3 | F1 | F1 | F1 | 0 | F1 | 0 |
| | 1 | 0 | 0 | 0 | 0 | 0 | 0 |
| XXV | 3 | F1 | 0 | F1 | F1 | F1 | 0 |
| | 1 | 0 | 0 | 0 | 0 | 0 | 0 |
| Comments | | more tillers | more fruit set | more fruit set, tillers | more fruit set, tillers | more fruit set, tillers | more fruit set |

| Species | Appl'n. Rate (lb/A) | Compound Nos. | | | | | |
|---|---|---|---|---|---|---|---|
| | | 4704 | 4705 | 4707 | 4708 | 4709 | 4710 |
| I | 3 | F3G3 | F3G3 | F3G3 | F3G3 | F3G3 | F3G3 |
| | 1 | F3G2 | F3G3 | F3G3 | F3G3 | F3G3 | F3G3 |

TABLE 3-continued
POST-EMERGENT EFFECTS ON 24 SPECIES

| | | | | | | | |
|---|---|---|---|---|---|---|---|
| II | 3 | F3G3 | F3G3 | F3G3 | F3G3 | F3G3 | F3G3 |
| | 1 | F3G2 | F3G3 | F3G3 | F3G3 | F3G3 | F3G3 |
| III | 3 | F1 | F2G1 | F3G2 | F3G2 | F3G2 | F3G3 |
| | 1 | 0 | 0 | F1G1 | F1G1 | F1G1 | F1G1 |
| IV | 3 | G1 | G1 | G1 | G1 | G1 | G1 |
| | 1 | 0 | 0 | 0 | 0 | 0 | 0 |
| V | 3 | F1G1 | F2G2 | F2G2 | F2G2 | F3G2 | F3G2 |
| | 1 | 0 | F1 | F1 | F2G1 | F1 | F2 |
| VI | 3 | 0 | 0 | 0 | 0 | 0 | 0 |
| | 1 | 0 | 0 | 0 | 0 | 0 | 0 |
| VII | 3 | 0 | 0 | F1 | 0 | F1 | F1 |
| | 1 | 0 | 0 | 0 | 0 | 0 | 0 |
| VIII | 3 | N3G2 | F1 | F2G1 | F2 | F2 | F2G1 |
| | 1 | NqF1 | F1 | F2 | F1 | F1 | F1 |
| IX | 3 | N4 | F3G3 | F3G3 | F3G3 | F3G3 | F3G3 |
| | 1 | F3G2 | F3G2 | F3G2 | F3G2 | F3G2 | F3G2 |
| X | 3 | F3G3 | F3G3 | F3G3 | F3G3 | C3F3G3 | F3G3C3 |
| | 1 | F2G2 | F3G2 | F3C2 | F3G2C2 | F2G2C2 | F3G2C2 |
| XI | 3 | F1 | F1 | F1 | F1 | F2G1 | F2G1 |
| | 1 | 0 | 0 | 0 | 0 | 0 | F1 |
| XII | 3 | N4 | C3F2 | C3G3 | C3G2 | C3G3 | C3G3 |
| | 1 | N2F2 | F1C1 | C2F1 | C2F1 | C2F1 | C2F1 |
| XIII | 3 | N3F3 | F3G2 | F3G2 | F3 | F3C1 | F3G1 |
| | 1 | N2F2 | F3 | F3 | F3 | F3 | F3 |
| XIV | 3 | F1N1 | — | — | F1 | F1 | — |
| | 1 | F1 | F2 | F1 | F1 | F1 | F1 |
| XV | 3 | F3G3 | F2G2 | F3G3 | F3G2 | F3G3 | F3G3 |
| | 1 | F2 | F2G2 | F2 | F2G1 | F2G1 | F2G2 |
| XVI | 3 | F3G3 | F3G3 | F3G3 | F3G3 | F3G3 | F3G3 |
| | 1 | F3G2 | F3G3 | F3G3 | F3G3 | F3G3 | F3G3 |
| XVII | 3 | 0 | F1G1 | F2G1 | F1 | F2G1 | F2G1 |
| | 1 | 0 | 0 | 0 | 0 | F1 | F1 |
| XVIII | 3 | F2G1 | F2G2 | F2G2 | F3G2 | F2G2 | F2G2 |
| | 1 | F1 | F1 | F1 | F1 | F1G1 | F1 |
| XIX | 3 | F3G3 | F3G2 | F3G3 | F3G3 | F3G3 | F3G3 |
| | 1 | F1N1 | F3G1 | F3G1 | F2G1 | F2G1 | F3G2 |
| XX | 3 | F1 | F1 | F1 | F1 | F1 | F2G1 |
| | 1 | 0 | 0 | F1 | F1 | 0 | F1 |
| XXI | 3 | F3G2 | F2G1 | F2G1 | F2G1 | F2G1 | F3G2 |
| | 1 | F1 | F1 | F1 | F1 | F1 | F2 |
| XXII | 3 | F3G2 | F2G1 | F2G1 | F2G2 | F2G1 | F3G2 |
| | 1 | F1 | F1 | F2 | F2 | F1 | F2 |
| XXIII | 3 | N1G1 | F1 | F1 | F1 | F1 | F1 |
| | 1 | 0 | 0 | F1 | F1 | 0 | 0 |
| XXIV | 3 | N1G1 | F1 | F1 | F1 | F1 | F2 |
| | 1 | 0 | F1 | F1 | F1 | F1 | F1 |
| XXV | 3 | N1G1 | F2 | F1 | F1 | F1 | C1F1 |
| | 1 | 0 | 0 | F1 | 0 | 0 | 0 |
| Comments | | more fruit set | more fruit set, tillers | more fruit set, tillers | more fruit set, tillers | more fruit set, tillers | more fruit set, tillers |

| Species | Appl'n. Rate (lb/A) | Compound Nos. | | | | | |
|---|---|---|---|---|---|---|---|
| | | 4716 | 4717 | 4718 | 4719 | 4720 | 4721 |
| I | 3 | F3G3 | F3G3 | F3G3 | F1 | F3G3 | F1 |
| | 1 | F3G3 | F3G3 | F3G3 | 0 | F3G2 | 0 |
| II | 3 | F3G3 | F3G3 | F3G3 | F1 | F3G3 | F1 |
| | 1 | F3G3 | F3G2 | F3G3 | 0 | F3G3 | 0 |
| III | 3 | F2G1 | F2G1 | F1G1 | 0 | F2G1 | 0 |
| | 1 | F1 | F1 | F1 | 0 | F1G1 | 0 |
| IV | 3 | F1 | 0 | 0 | 0 | 0 | 0 |
| | 1 | 0 | 0 | 0 | 0 | 0 | 0 |
| V | 3 | F3G2 | F3G2 | F2G1 | 0 | F2G2 | 0 |
| | 1 | F1 | F1 | F1 | 0 | F1 | 0 |
| VI | 3 | 0 | 0 | 0 | 0 | 0 | 0 |
| | 1 | 0 | 0 | 0 | 0 | 0 | 0 |
| VII | 3 | F1 | F1 | 0 | 0 | F1 | 0 |
| | 1 | 0 | 0 | 0 | 0 | 0 | 0 |
| VIII | 3 | F1 | F2 | F1 | 0 | F2 | 0 |
| | 1 | F1 | 0 | F1 | 0 | F1 | 0 |
| IX | 3 | F3G3 | F3G3 | F3G3 | F1 | F3G3 | F1 |
| | 1 | F3G2 | F3G1 | F3G3 | F1 | F3G2 | F1 |
| X | 3 | F3G3 | F3G3 | F3G3C2 | F1 | F3G3C3 | F1 |
| | 1 | F2G2C1 | F2G1 | F3C2 | 0 | F2G2C1 | F1 |
| XI | 3 | F1G1 | F2G2 | F2G1 | 0 | F1G1 | 0 |
| | 1 | F1 | F1 | F1 | 0 | F1 | 0 |
| XII | 3 | F1G1 | C1F2G2 | F2C2 | 0 | F3C3G2 | 0 |
| | 1 | F1C1 | F1C1 | F1C1 | 0 | F2C2G1 | 0 |
| XIII | 3 | F3G1 | F3G1 | F3G1 | F1 | F3 | F1 |

TABLE 3-continued
POST-EMERGENT EFFECTS ON 24 SPECIES

|  | | | | | | | |
|---|---|---|---|---|---|---|---|
|  | 1 | F3 | F3 | F3 | 0 | F2 | 0 |
| XIV | 3 | F1 | F2 | — | 0 | — | 0 |
|  | 1 | F1 | F1 | F1 | 0 | F1 | 0 |
| XV | 3 | F2G2 | F3G3 | F3G2 | 0 | F3G2 | 0 |
|  | 1 | F2G1 | F2G1 | F2G2 | 0 | F2G1 | 0 |
| XVI | 3 | F3G3 | F3G3 | F3G3 | 0 | F3G3 | F1 |
|  | 1 | F3G3 | F3G3 | F3G3 | 0 | F3G3 | 0 |
|  | 3 | F1 | F1 | F1 | 0 | F2G1 | 0 |
|  | 1 | 0 | 0 | 0 | 0 | 0 | 0 |
| XVIII | 3 | F1 | F2G1 | F1G1 | 0 | F3G2 | 0 |
|  | 1 | F1 | F1 | F1 | 0 | F2G1 | 0 |
| XIX | 3 | F3G2 | F3G1 | F3G2 | F1 | F3G3C1 | F1 |
|  | 1 | F3 | F2C1 | F2C1 | 0 | F3C1 | 0 |
| XX | 3 | F1 | F1 | F1 | 0 | F1 | 0 |
|  | 1 | 0 | 0 | 0 | 0 | F1 | 0 |
| XXI | 3 | F2 | F2 | F2 | 0 | F2G1 | 0 |
|  | 1 | F1 | F1 | F1 | 0 | F1 | 0 |
| XXII | 3 | F2 | F2 | F2 | 0 | F2G1 | 0 |
|  | 1 | F1 | F1 | F1 | 0 | F1 | 0 |
| XXIII | 3 | 0 | 0 | 0 | 0 | F2G1 | 0 |
|  | 1 | 0 | 0 | 0 | 0 | 0 | 0 |
| XXIV | 3 | F1 | F1 | F1 | 0 | F1 | 0 |
|  | 1 | F1 | F1 | F1 | 0 | F1 | 0 |
| XXV | 3 | F1 | F1 | F2 | 0 | F1G1C1 | 0 |
|  | 1 | 0 | 0 | F1 | 0 | 0 | 0 |
| Comments |  | more fruit set, tillers | more fruit set, tillers | more fruit set, tillers | more fruit set | more fruit set, tillers | more fruit set |

| Species | Appl'n. Rate (lb/A) | Compound Nos. | | | | | |
|---|---|---|---|---|---|---|---|
|  |  | 4722 | 4723 | 4724 | 4725 | 4726 | 4727 |
| I | 3 | F1 | F1G1 | F3G3 | F3G3 | 0 | F3G2 |
|  | 1 | 0 | 0 | F1 | F3G3 | 0 | G1 |
| II | 3 | F1 | 0 | F3G3 | F3G3 | 0 | F1G1 |
|  | 1 | F1 | 0 | F2G1 | F3G3 | 0 | 0 |
| III | 3 | 0 | 0 | 0 | F2G2 | 0 | 0 |
|  | 1 | 0 | 0 | 0 | F1G1 | 0 | 0 |
| IV | 3 | 0 | 0 | 0 | G1 | 0 | 0 |
|  | 1 | 0 | 0 | 0 | 0 | 0 | 0 |
| V | 3 | 0 | 0 | 0 | F2G2 | 0 | 0 |
|  | 1 | 0 | 0 | 0 | F1 | 0 | 0 |
| VI | 3 | 0 | 0 | 0 | 0 | 0 | 0 |
|  | 1 | 0 | 0 | 0 | 0 | 0 | 0 |
| VII | 3 | 0 | 0 | 0 | 0 | 0 | 0 |
|  | 1 | 0 | 0 | 0 | 0 | 0 | 0 |
| VIII | 3 | 0 | 0 | 0 | F1 | F1 | N1 |
|  | 1 | 0 | 0 | 0 | 0 | 0 | 0 |
| IX | 3 | G1F2 | F2G2 | F3G3 | F3G3 | F2G1 | F3G3 |
|  | 1 | F1 | F1 | F3G2 | F3G3 | F1 | F3G1 |
| X | 3 | F2 | F1 | F3G3C1 | F3G3C2 | F1C1 | F2G2 |
|  | 1 | F1 | F1 | F2G1 | F2G2C1 | 0 | F2 |
| XI | 3 | 0 | 0 | F1 | F2G2 | 0 | 0 |
|  | 1 | 0 | 0 | 0 | F1 | 0 | 0 |
| XII | 3 | 0 | 0 | F1 | F3G2C2 | 0 | F1 |
|  | 1 | 0 | 0 | 0 | F1C1 | 0 | 0 |
| XIII | 3 | F3 | F2 | F3 | F3G3 | F1 | F3 |
|  | 1 | F2 | F2 | F3 | F3G2 | F1 | F2 |
| XIV | 3 | 0 | 0 | F1 | F2 | 0 | 0 |
|  | 1 | 0 | 0 | 0 | F1 | 0 | 0 |
| XV | 3 | F1 | 0 | F2G1 | F2G2 | 0 | F1 |
|  | 1 | 0 | 0 | F1 | F2G1 | 0 | 0 |
| XVI | 3 | F1 | 0 | F2G2 | F3G3 | F1 | N1F2 |
|  | 1 | 0 | 0 | F2 | F3G2 | 0 | N1 |
| XVII | 3 | 0 | 0 | 0 | F1 | 0 | 0 |
|  | 1 | 0 | 0 | 0 | 0 | 0 | 0 |
| XVIII | 3 | 0 | 0 | F1 | F3G2 | 0 | 0 |
|  | 1 | 0 | 0 | 0 | F2G1 | 0 | 0 |
| XIX | 3 | F1 | F1 | F3G2 | F3G3 | F1 | F2 |
|  | 1 | 0 | F1 | F2 | F3G2 | 0 | F1 |
| XX | 3 | 0 | 0 | 0 | F1 | 0 | 0 |
|  | 1 | 0 | 0 | 0 | 0 | 0 | 0 |
| XXI | 3 | 0 | 0 | 0 | F2G1 | 0 | 0 |
|  | 1 | 0 | 0 | 0 | F2 | 0 | 0 |
| XXII | 3 | 0 | 0 | 0 | F2G1 | 0 | 0 |
|  | 1 | 0 | 0 | 0 | F2 | 0 | 0 |
| XXIII | 3 | 0 | 0 | 0 | 0 | 0 | 0 |
|  | 1 | 0 | 0 | 0 | 0 | 0 | 0 |
| XXIV | 3 | 0 | 0 | 0 | F1 | 0 | 0 |
|  | 1 | 0 | 0 | 0 | 0 | 0 | 0 |

TABLE 3-continued
POST-EMERGENT EFFECTS ON 24 SPECIES

| | | | | | | | |
|---|---|---|---|---|---|---|---|
| XXV | 3 | 0 | 0 | 0 | 0 | 0 | 0 |
| | 1 | 0 | 0 | 0 | 0 | 0 | 0 |
| Comments | | more fruit set | more fruit set | | more fruit set | more fruit set | |

| Species | Appl'n. Rate (lb/A) | 4728 | 4739 | 4740 | 4741 | 4742 | 4743 |
|---|---|---|---|---|---|---|---|
| I | 3 | F3G3 | F3G3 | F3G2 | F1G1 | F3G3 | F3G3 |
| | 1 | G3F3 | F3G3 | F2G2 | F1G1 | F3G2 | F1G1 |
| II | 3 | F3G3 | F3G3 | F3G2 | F1G1 | F3G3 | F3G3 |
| | 1 | F3G2 | F3G3 | F2B2 | F1 | F1G1 | F1G1 |
| III | 3 | F2G2 | F2G1 | 0 | 0 | F2G2 | 0 |
| | 1 | F1 | F1 | 0 | 0 | 0 | 0 |
| IV | 3 | F3G2 | 0 | 0 | 0 | 0 | 0 |
| | 1 | F2G2 | 0 | 0 | 0 | 0 | 0 |
| V | 3 | F2G2 | F2G2 | 0 | 0 | 0 | 0 |
| | 1 | 0 | F1 | 0 | 0 | 0 | 0 |
| VI | 3 | 0 | C1 | 0 | 0 | 0 | 0 |
| | 1 | 0 | 0 | 0 | 0 | 0 | 0 |
| VII | 3 | 0 | F1 | 0 | 0 | 0 | 0 |
| | 1 | 0 | 0 | 0 | 0 | 0 | 0 |
| VIII | 3 | 0 | F1 | 0 | 0 | 0 | 0 |
| | 1 | 0 | 0 | 0 | 0 | 0 | 0 |
| IX | 3 | F3G3 | F3G3 | F2G1 | G1F2 | F3G3 | F3G2 |
| | 1 | F3G3 | F3G3 | F1 | F2G1 | F3G3 | F2G1 |
| X | 3 | F3G3C2 | F3G2C2 | F2 | F2 | F3G2 | F1 |
| | 1 | F3G1 | F2G2 | F1 | F1 | F2G1 | F1 |
| XI | 3 | F1 | F1 | F1 | 0 | 0 | 0 |
| | 1 | 0 | F1 | 0 | 0 | 0 | 0 |
| XII | 3 | F2G2C1 | F1G1 | C1 | 0 | F1 | F1 |
| | 1 | F1C1 | F1C1 | 0 | 0 | 0 | 0 |
| XIII | 3 | F3G3 | F3G1 | F3 | F2 | F3 | F3 |
| | 1 | F3G3 | F3 | F1 | F1 | F3 | F2 |
| XIV | 3 | F2 | F1 | 0 | 0 | 0 | 0 |
| | 1 | F1 | 0 | 0 | 0 | 0 | 0 |
| XV | 3 | F3G3 | F2G2 | N2F1 | N3F2 | N3G3 | N1 |
| | 1 | F3G2 | F2G1 | 0 | N1 | N1G1 | 0 |
| XVI | 3 | F3G3 | F3G3 | F1 | F1 | F3G3 | F1 |
| | 1 | F3G3 | F3G3 | 0 | 0 | F2 | 0 |
| XVII | 3 | F1 | F1 | 0 | 0 | 0 | 0 |
| | 1 | 0 | F1 | 0 | 0 | 0 | 0 |
| XVIII | 3 | F2G2 | F2G2 | 0 | 0 | 0 | 0 |
| | 1 | F1G1 | F1 | 0 | 0 | 0 | 0 |
| XIX | 3 | F3G3 | F3G3 | F1 | F1 | F3G1 | C1F1 |
| | 1 | F3G3C2 | F3G2 | F1 | 0 | F2 | C1F1 |
| XX | 3 | C1 | F1 | 0 | 0 | 0 | 0 |
| | 1 | 0 | 0 | 0 | 0 | 0 | 0 |
| XXI | 3 | F2G1 | F2 | 0 | 0 | 0 | 0 |
| | 1 | F1 | F1 | 0 | 0 | 0 | 0 |
| XXII | 3 | F2G1 | F2 | 0 | 0 | 0 | 0 |
| | 1 | F1 | F1 | 0 | 0 | 0 | 0 |
| XXIII | 3 | 0 | G1 | 0 | 0 | 0 | 0 |
| | 1 | 0 | 0 | 0 | 0 | 0 | 0 |
| XXIV | 3 | F1 | F1 | 0 | 0 | 0 | 0 |
| | 1 | 0 | 0 | 0 | 0 | 0 | 0 |
| XXV | 3 | 0 | F1C1 | 0 | 0 | 0 | 0 |
| | 1 | 0 | F0 | 0 | 0 | 0 | 0 |
| Comments | | more fruit set | more fruit set | more fruit set | more fruit set | more fruit set | more fruit set |

| Species | Appl'n. Rate (lb/A) | 4756 | 4758 | 4759 | 4760 | 4762 | 4764 | 4850 |
|---|---|---|---|---|---|---|---|---|
| I | 3 | F3G3 | F1G1 | 0 | 0 | F3G2 | F3G3 | F3G3 |
| | 1 | F2G1 | 0 | 0 | 0 | F2G1 | F3G2 | F3G3 |
| II | 3 | F3G3 | F1G1 | F1 | 0 | F2G2 | F3G3 | F3G3 |
| | 1 | F2 | 0 | 0 | 0 | F1 | F3G3 | F3G2 |
| III | 3 | 0 | 0 | 0 | 0 | 0 | F1G1 | 0 |
| | 1 | 0 | 0 | 0 | 0 | 0 | 0 | 0 |
| IV | 3 | 0 | 0 | 0 | 0 | 0 | 0 | 0 |
| | 1 | 0 | 0 | 0 | 0 | 0 | 0 | 0 |
| V | 3 | F1 | 0 | 0 | 0 | 0 | F2G1 | 0 |
| | 1 | 0 | 0 | 0 | 0 | 0 | C1 | 0 |
| VI | 3 | 0 | 0 | 0 | 0 | 0 | 0 | 0 |
| | 1 | 0 | 0 | 0 | 0 | 0 | 0 | 0 |
| VII | 3 | 0 | 0 | 0 | 0 | 0 | F1 | 0 |
| | 1 | 0 | 0 | 0 | 0 | 0 | F1 | 0 |

TABLE 3-continued
POST-EMERGENT EFFECTS ON 24 SPECIES

| | | | | | | | | |
|---|---|---|---|---|---|---|---|---|
| VIII | 3 | F2 | N1 | 0 | 0 | F1 | F2G1 | N1 |
| | 1 | F1 | 0 | 0 | 0 | 0 | F2 | 0 |
| IX | 3 | F3G3 | F2G2 | 0 | 0 | F1 | F3G3 | F3G3 |
| | 1 | F2 | F2 | 0 | 0 | F1 | F3G2 | F3 |
| X | 3 | F2 | F1 | F1 | F1 | F1 | F3G3C3 | F2G1 |
| | 1 | F2 | 0 | 0 | F1 | F1 | F2G2 | F2 |
| XI | 3 | F1G1 | 0 | 0 | 0 | 0 | F1C1 | F1 |
| | 1 | 0 | 0 | 0 | 0 | 0 | F1 | 0 |
| XII | 3 | F2 | 0 | G1 | 0 | 0 | F3G2C2 | — |
| | 1 | 0 | 0 | 0 | 0 | 0 | F1C1 | F1G1 |
| XIII | 3 | F3 | F3 | N1 | N1F1 | F1 | F3C2 | F3G1 |
| | 1 | F2 | F2 | 0 | 0 | 0 | F3 | F3 |
| XIV | 3 | F2 | 0 | 0 | 0 | 0 | F2G1 | F1 |
| | 1 | 0 | 0 | 0 | 0 | 0 | F1 | F1 |
| XV | 3 | F2 | N1 | 0 | 0 | F1 | F3G2 | F2G1 |
| | 1 | F1 | 0 | 0 | 0 | 0 | F2G1 | F2 |
| XVI | 3 | F2 | N1F1 | N1 | F1 | F1 | F3G3 | F3G3 |
| | 1 | F1 | 0 | 0 | 0 | F1 | F3G3 | F3G3 |
| XVII | 3 | F2G1 | 0 | 0 | 0 | 0 | F1 | 0 |
| | 1 | 0 | 0 | 0 | 0 | 0 | 0 | 0 |
| XVIII | 3 | F2 | 0 | 0 | 0 | 0 | F2G1 | F1G1 |
| | 1 | 0 | 0 | 0 | 0 | 0 | F1 | 0 |
| XIX | 3 | F2 | 0 | 0 | F1 | F2 | F3G2 | F3G3 |
| | 1 | F1 | 0 | 0 | 0 | F1 | F2 | F3 |
| XX | 3 | 0 | 0 | 0 | 0 | 0 | C1 | 0 |
| | 1 | 0 | 0 | 0 | 0 | 0 | 0 | 0 |
| XXI | 3 | F1 | 0 | 0 | 0 | 0 | 0 | 0 |
| | 1 | 0 | 0 | 0 | 0 | 0 | 0 | 0 |
| XXII | 3 | F1 | 0 | 0 | 0 | 0 | 0 | 0 |
| | 1 | 0 | 0 | 0 | 0 | 0 | 0 | 0 |
| XXIII | 3 | 0 | 0 | 0 | 0 | 0 | F1 | F1 |
| | 1 | 0 | 0 | 0 | 0 | 0 | 0 | 0 |
| XXIV | 3 | 0 | 0 | 0 | 0 | 0 | F2 | F1 |
| | 1 | 0 | 0 | 0 | 0 | 0 | 0 | 0 |
| XXV | 3 | 0 | 0 | 0 | 0 | 0 | F1 | 0 |
| | 1 | 0 | 0 | 0 | 0 | 0 | 0 | 0 |
| Comments | | | | | | | more tillers | |

| Species | Appl'n. Rate (lb/A) | 4956 | 4957 | 4958 | 4959 |
|---|---|---|---|---|---|
| I | 3 | F3G3 | F3G3 | F3G3 | F3G3 |
| | 1 | F2G2 | F3G3 | F3G2 | F3G3 |
| II | 3 | F3G3 | F3G3 | F3G3 | F3G3 |
| | 1 | F2G2 | F3G3 | F3G3 | F3G3 |
| III | 3 | F1G1 | F2G1 | F2G2 | F2G1 |
| | 1 | 0 | 0 | G1F1 | F1 |
| IV | 3 | G1 | F1G1 | F1G1 | G1 |
| | 1 | 0 | 0 | 0 | 0 |
| V | 3 | F2G1 | F2G2 | F3G2 | F2G2 |
| | 1 | 0 | F1 | F2G1 | F1 |
| VI | 3 | 0 | 0 | 0 | 0 |
| | 1 | 0 | 0 | 0 | 0 |
| VII | 3 | F1 | F1 | F1 | F1 |
| | 1 | 0 | 0 | F1 | 0 |
| VIII | 3 | F2 | F3G1 | F3G2 | F3G2 |
| | 1 | F1 | F1 | F2 | F1 |
| IX | 3 | F3G2 | F3G3 | F3G3 | F3G3 |
| | 1 | F3 | F3G2 | F3G3 | F3G3 |
| X | 3 | F3G2 | F3G2 | F3G3 | F3G3 |
| | 1 | F2G1 | F2G2 | F3G2 | F2G2 |
| XI | 3 | F3G3 | F3G3 | F3G3 | F3G2 |
| | 1 | F2G1 | F1G1 | F2G2 | F2G2 |
| XII | 3 | F2G1 | F3G2 | F3G3 | F3G3 |
| | 1 | F1 | F2G1 | F3G2 | F2G2 |
| XIII | 3 | F3E3 | F3G3 | F3G3 | F3G3 |
| | 1 | F3#2 | F3E1 | F3E3 | F3E2 |
| XIV | 3 | F1 | F2 | F2 | F2 |
| | 1 | F1 | F1 | F2 | F2 |
| XV | 3 | F2G2 | F2G2 | F3G2 | F2G2 |
| | 1 | F2G1 | F2G1 | F3G2 | F2G2 |
| XVI | 3 | F3G3 | F3G3 | F3G3 | F3G3 |
| | 1 | F3G2 | F3G3 | F3G3 | F3G3 |
| XVII | 3 | F1G1 | F1 | F2 | F1 |
| | 1 | F1 | F1 | F1 | F1 |
| XVIII | 3 | F2G1 | F2G2 | F3G2 | F2G1 |
| | 1 | F1 | F1 | F2 | F1 |
| XIX | 3 | F3G2 | F3G3 | F3G3 | F3G3 |
| | 1 | F3G1 | F3G1 | F2G1 | F2G2 |
| XX | 3 | F1 | F1 | F1 | F1 |

TABLE 3-continued

POST-EMERGENT EFFECTS ON 24 SPECIES

|      |   |    | F1 F1 | 0    |     |
|------|---|----|-------|------|-----|
| XXI  | 3 | F2 | F2    | F3G1 | F2  |
|      | 1 | F1 | F1    | F2   | F1  |
| XXII | 3 | F2 | F2    | F3G1 | F2  |
|      | 1 | F1 | F1    | F2   | F1  |
| XXIII| 3 | F1 | F1    | F2G2 | F1G1|
|      | 1 | 0  | F1    | F1G1 | 0   |
| XXIV | 3 | F1 | F1    | F1   | F1  |
|      | 1 | 0  | F1    | F1   | F1  |
| XXV  | 3 | F1 | F1    | F1   | F1  |
|      | 1 | 0  | F1    | F1   | 0   |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor El-719), 20 wt. percent xylene and 20 wt. percent deodorized kerosene, then bringing total volume up to 80 ml. by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The extent of growth regulatory effect on the plants was estimated on a scale of 0 to 10 and is also recorded in the following table:

TABLE 4

GROWTH REGULATING EFFECTS ON TWO SPECIES

|              |             | TOMATO                      |                         | SOYBEAN                     |                         |
|--------------|-------------|-----------------------------|-------------------------|-----------------------------|-------------------------|
| Compound No. | Rate oz/A.  | G.R. Effect 2 Rep. Avg.     | Fruit Increase % of Check | G.R. Effect 2 Rep. Avg.     | Pod Increase % of Check |
| 4368         | 16          | 6.5                         | 150                     | 7.5                         | 203                     |
|              | 4           | 4.5                         | 236                     | 4                           | 155                     |
|              | 1           | 2.5                         | 192                     | 3                           | 121                     |

The information presented in tabular form herein will enable a worker in the art to make a selection from among the growth regulator compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulator compounds are usually applied in combination with inert carriers or diluents, as in aqueous sprays, granules and dust formulations in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulators are applied in formulations which desirably contain from 0.1 percent to 95 percent of a compound of formula (1) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a non-phytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

I claim:

1. The method of regulating the growth of plants comprising applying to the plants, the seed or the soil an effective amount of a compound having one of the following structural formulas;

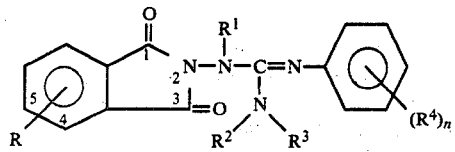
(1a)

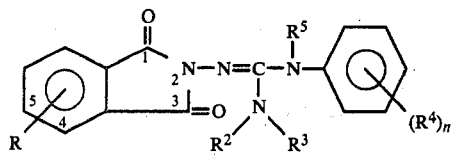
(1b)

in which R, $R^1$ and $R^5$ are hydrogen or $C_1$ to $C_5$ alkyl, $R^2$ and $R^3$ are alike or unlike, one of which may be hydrogen but otherwise are substituents selected from branched or unbranched $C_1$ to $C_5$ alkyl, alkenyl, alkynyl, $C_2$ to $C_5$ hydroxyalkyl or alkoxyalkyl, $C_3$ to $C_5$ cycloalkyl, furfuryl, pyridyl, benzyl, phenyl, $C_1$ to $C_5$ alkyl-substituted phenyl, or $-NR^2R^3$ together may be 2,5-dimethyl-1-pyrryl, 4-morpholinyl, or 1-pyrrolidinyl, $R^4$ is halogen, nitro, cyano, trifluoromethyl or $C_1$ to $C_5$ alkyl and n is zero, one or two.

2. The method of regulating the growth of plants comprising applying to the plants, the seed or the soil an effective amount of a compound having one of the following structural formulas:

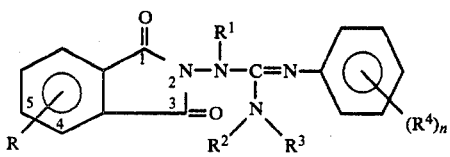
(1a)

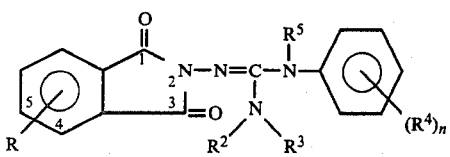
(1b)

in which R is H, $R^1$ is $CH_3$, $-NR^2R^3$ is -1-piperidyl, $R^5$ is hydrogen or $C_1$ to $C_5$ alkyl and n is zero.

3. The method of regulating the growth of plants comprising applying to the plants, the seed or the soil an effective amount of a compound having one of the following structural formulas:

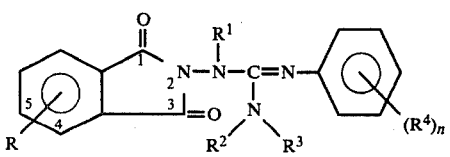
(1a)

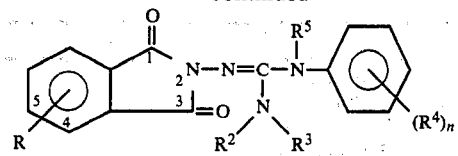
(1b)

in which R is H, $R^1$ is $CH_3$, $-NR^2R^3$ is $-N(nonyl)_2$, $R^5$ is hydrogen or $C_1$ to $C_5$ alkyl and n is zero.

4. The method of regulating the growth of plants comprising applying to the plants, the seed or the soil an effective amount of a compound having one of the following structural formulas:

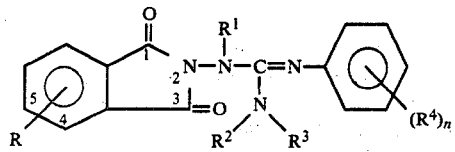
(1a)

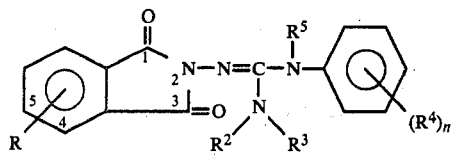
(1b)

in which R is H, $R^1$ is $CH_3$, $-NR^2R^3$ is $-N$-methylcyclooctyl, $R^5$ is hydrogen or $C_1$ to $C_5$ alkyl and n is zero.

5. The method of regulating the growth of plants comprising applying to the plants, the seed or the soil an effective amount of a compound having one of the following structural formulas:

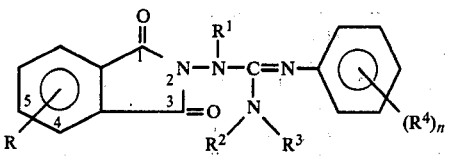
(1a)

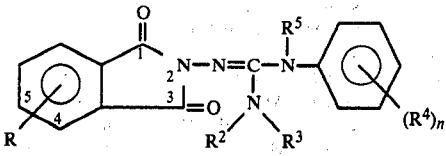
(1b)

in which R is H, $R^1$ is $CH_3$, $-NR^2R^3$ is $-N(octyl)_2$, $R^5$ is hydrogen or $C_1$ to $C_5$ alkyl and n is zero.

6. The method of regulating the growth of plants which comprises applying to the plants pre- or post-emergently an effective amount of a composition comprising from 0.1 to 95 weight percent of a compound as specified in claim 1 in combination with a carrier or surface active agent.

7. The method of increasing fruit set of crop plants which comprises applying to the plant foliage an effective amount of a compound as specified in claim 1 in combination with an inert carrier and a surface active agent.

8. The method of regulating the growth of plants which comprises applying to the plants, a compound as specified in claim 1 in which the substituents represented by R, $R^1$, $-NR^2R^3$ and $(R^4)n$ are those tabulated below:

| R | R$^1$ | —NR$^2$R$^3$ | (R$^4$)$_n$ |
|---|---|---|---|
| H | CH$_3$ | —N(C$_2$H$_5$)$_2$ | n = o |
| H | CH$_3$ | —N(CH$_3$)$_2$ | n = o |
| H | CH$_3$ | -4-morpholinyl | n = o |
| H | CH$_3$ | -1-pyrrolidinyl | n = o |
| H | CH$_3$ | —N—methyl benzyl | n = o |
| H | CH$_3$ | —N—isopropyl benzyl | n = o |
| H | CH$_3$ | —N—methyl phenyl | n = o |
| H | CH$_3$ | —N—ethyl phenyl | n = o |
| H | CH$_3$ | —N—(CH$_2$CH$_2$CH$_3$)$_2$ | n = o |
| H | CH$_3$ | —N(isopropyl)$_2$ | n = o |
| H | CH$_3$ | —N(CH$_2$CH$_2$CH$_2$CH$_3$)$_2$ | n = o |
| H | CH$_3$ | —N—propyl phenyl | n = o |
| H | CH$_3$ | —N(sec. butyl)$_2$ | n = o |
| H | CH$_3$ | —N(CH$_2$CH$_2$CH$_2$CH$_2$CH$_3$)$_2$ | n = o |
| H | CH$_3$ | —N(allyl)$_2$ | n = o |
| H | CH$_3$ | —N(isobutyl)$_2$ | n = o |
| H | CH$_3$ | —N—methyl propyl | n = o |
| H | CH$_3$ | —N—propyl isopropyl | n = o |
| H | CH$_3$ | —N—propyl isobutyl | n = o |
| H | CH$_3$ | —N—propyl sec. butyl | n = o |
| H | CH$_3$ | —N—propyl butyl | n = o |
| H | CH$_3$ | —N—benzyl 2-propenyl | n = o |
| H | CH$_3$ | —N—allyl phenyl | n = o |
| H | CH$_3$ | —N—ethyl p-tolyl | n = o |
| H | CH$_3$ | -4-morpholinyl | 3-fluoro |
| H | CH$_3$ | —NH—CH$_2$CH$_2$CH$_2$CH$_3$ | n = o |
| H | CH$_3$ | —NH—C(CH$_3$)$_3$ | n = o |
| H | CH$_3$ | —NH—cyclopropyl | n = o |
| H | CH$_3$ | —NH—cyclopentyl | n = o |
| H | CH$_3$ | —N(CH$_3$)(CH$_2$CH$_2$OH) | n = o |
| H | CH$_3$ | —N(CH$_3$)$_2$ | 2,5-dimethyl |
| H | CH$_3$ | —N(CH$_3$)$_2$ | 4-nitro |
| H | CH$_3$ | —N(CH$_3$)$_2$ | 4-fluoro |
| H | CH$_3$ | —N(CH$_3$)$_2$ | 4-cyano |
| H | CH$_3$ | —N(CH$_3$)$_2$ | 4-CF$_3$ |
| H | H | —N(CH$_3$)$_2$ | 3-fluoro |

-continued

| R | R$^1$ | —NR$^2$R$^3$ | (R$^4$)$_n$ |
|---|---|---|---|
| H | CH$_3$ | 1-pyrrolidinyl | 3-fluoro |
| 4-CH$_3$ | CH$_3$ | —NHCH$_2$CH$_2$CH$_3$ | n = o |
| H | CH$_3$ | —NH—CH$_2$CH$_2$OCH$_3$ | n = o |
| H | CH$_3$ | —N—methyl furfuryl | n = o |
| H | CH$_3$ | -2,5-dimethyl-1-pyrryl | n = o |
| H | CH$_3$ | —NH—2-pyridyl | n = o. |

9. The method of claim 7 in which the crop plants are of the species *Lycopersicum esculentum*.

10. The method of claim 7 in which the crop plants are of the species *Soja max*.

11. The method of regulating the growth of plants comprising applying to the plants, the seed or the soil an effective amount of a compound having one of the following structural formulas:

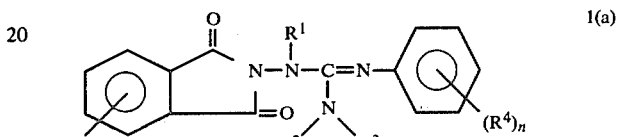

1(a)

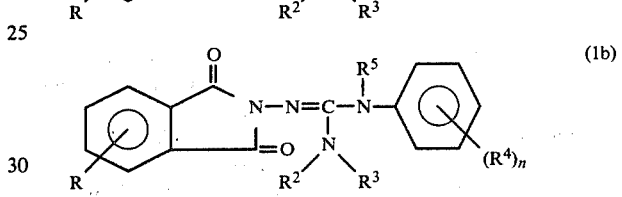

1(b)

in which R is hydrogen, R$^1$ is methyl, —NR$^2$R$^3$ is —N(CH$_3$)$_2$, (R$^4$)$_n$ is 3-acetyl, and R$^5$ is hydrogen or C$_1$ to C$_5$ alkyl.

* * * * *

UNITED STATES PATENT OFFICE
CERTIFICATE OF CORRECTION

Patent No. 4,404,017  Dated September 13, 1983

Inventor(s) Jerry L. Rutter

It is certified that error appears in the above-identified patent and that said Letters Patent are hereby corrected as shown below:

Col. 11, Table 3-continued (bottom section):
  Compound 4656 at Species XVI, 2nd line, "F3G2" should read --F3G3--;
  Compound 4657 at Species XVI, 2nd line, insert --F3G2-- in blank space;
  Compound 4655 at Species XVI, 3rd line, delete "F3G3";

Col. 23, Table 3-continued, the first line should read:
  -- 1    0    F1    F1    0 --;

Signed and Sealed this

Third Day of December 1985

[SEAL]

Attest:

DONALD J. QUIGG

Attesting Officer    Commissioner of Patents and Trademarks